US010052119B2

(12) United States Patent
Ueda et al.

(10) Patent No.: US 10,052,119 B2
(45) Date of Patent: *Aug. 21, 2018

(54) KNEE JOINT SURGICAL TREATMENT

(71) Applicant: OLYMPUS CORPORATION, Tokyo (JP)

(72) Inventors: Sohei Ueda, Tokyo (JP); Chie Onuma, Tama (JP); Manabu Ishikawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 321 days.

This patent is subject to a terminal disclaimer.

(21) Appl. No.: 14/878,684

(22) Filed: Oct. 8, 2015

(65) Prior Publication Data

US 2017/0100156 A1  Apr. 13, 2017

(51) Int. Cl.
*A61B 17/32* (2006.01)
*A61B 17/3205* (2006.01)

(52) U.S. Cl.
CPC .. *A61B 17/320068* (2013.01); *A61B 17/3205* (2013.01); *A61B 2017/320072* (2013.01)

(58) Field of Classification Search
CPC .............................................. A61B 17/320068
See application file for complete search history.

(56) References Cited

U.S. PATENT DOCUMENTS

| 6,544,260 B1 | 4/2003 | Markel et al. |
| 8,709,089 B2 | 4/2014 | Lang et al. |
| 2004/0068267 A1 | 4/2004 | Harvie et al. |
| 2005/0054954 A1 | 3/2005 | Lidgren et al. |
| 2006/0030871 A1 | 2/2006 | Hain et al. |
| 2006/0253050 A1 | 11/2006 | Yoshimine et al. |
| 2009/0018654 A1 | 1/2009 | Schmieding et al. |
| 2010/0121197 A1 | 5/2010 | Ota et al. |
| 2010/0174368 A1 | 7/2010 | Lynch et al. |
| 2010/0191173 A1 | 7/2010 | Kimura et al. |
| 2010/0298894 A1 | 11/2010 | Bojarski et al. |
| 2010/0312350 A1 | 12/2010 | Bonutti |
| 2011/0196401 A1 | 8/2011 | Robertson et al. |

(Continued)

FOREIGN PATENT DOCUMENTS

| JP | H05-168642 A | 7/1993 |
| JP | 2006-334268 A | 12/2006 |

OTHER PUBLICATIONS

U.S. Appl. No. 14/878,571, filed Oct. 8, 2015 in the name of Sohei Ueda, et al.

(Continued)

*Primary Examiner* — Andrew Yang
(74) *Attorney, Agent, or Firm* — Oliff PLC

(57) ABSTRACT

A surgical treatment of an ACL or a PCL of a knee joint under an arthroscope, includes: contacting a treating portion of an ultrasonic device with a start region to which the ACL or the PCL of a femur adheres, and excising the femur and a remaining ligament of the ACL, or the femur and a remaining ligament of the PCL by ultrasonically vibrating the treating portion, thereby exposing a footprint of the femur; and contacting the treating portion with an end region to which the ACL or the PCL of a tibia adheres, and excising the tibia and a remaining ligament of the ACL, or the tibia and a remaining ligament of the PCL by ultrasonically vibrating the treating portion, thereby exposing a footprint of the tibia.

3 Claims, 11 Drawing Sheets

(56) References Cited

U.S. PATENT DOCUMENTS

| | | |
|---|---|---|
| 2012/0165843 A1 | 6/2012 | Gannoe et al. |
| 2013/0006278 A1 | 1/2013 | Mayer et al. |
| 2013/0096471 A1 | 4/2013 | Slayton et al. |
| 2014/0230995 A1 | 8/2014 | Schlottig et al. |
| 2015/0165243 A1 | 6/2015 | Slayton et al. |
| 2016/0338782 A1 | 11/2016 | Bowling et al. |

OTHER PUBLICATIONS

U.S. Appl. No. 14/878,664, filed Oct. 8, 2015 in the name of Sohei Ueda, et al.
Nov. 28, 2017 Office Action issued in U.S Appl. No. 14/878,664.
Dec. 28, 2017 Office Action issued in U.S. Appl. No. 15/337,271.
U.S. Appl. No. 15/337,596, filed Oct. 28, 2016 in the name of Michio Takayama et al.
U.S. Appl. No. 15/337,271, filed Oct. 28, 2016 in the name of Sohei Ueda et al.
Jun. 5, 2018 Office Action Issued in U.S. Appl. No. 15/337,271.

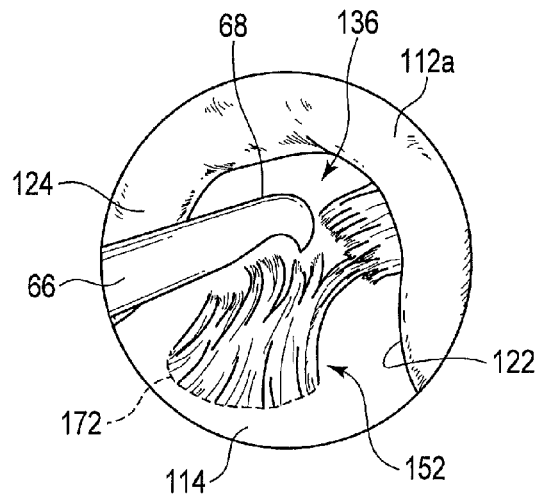
F I G. 12A
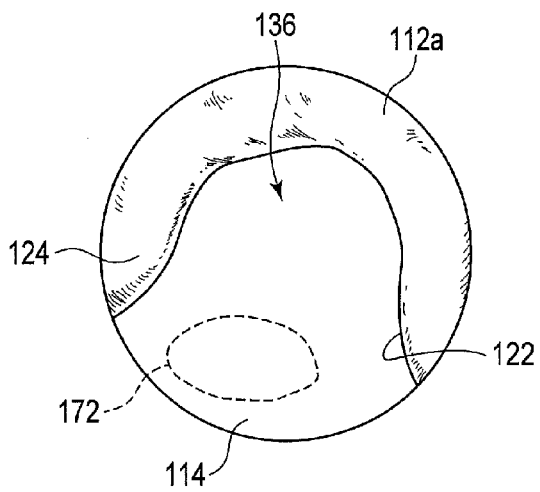
F I G. 12B
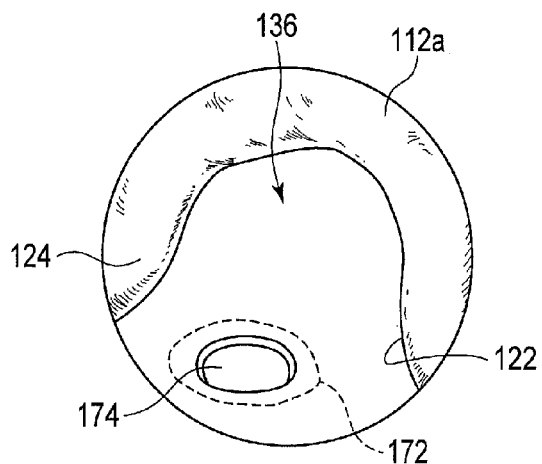
F I G. 12C

KNEE JOINT SURGICAL TREATMENT

BACKGROUND OF THE INVENTION

1. Field of the Invention

The present invention relates to a surgical treatment of a knee joint to be performed under an arthroscope.

2. Description of the Related Art

It is known that, when performing an arthroscopic surgical treatment for a patient's knee joint, a surgeon proceeds with the treatment while inserting and removing treatment devices through a portal many times in accordance with a tissue of a treatment region with the progress of the treatment, and the above treatment devices are, for example, a shaver to shave a soft tissue, an abrader burr to abrade a bone, or an RF device to excise the soft tissue while stopping bleeding.

BRIEF SUMMARY OF THE INVENTION

According to one aspect of the present invention, a surgical treatment of an anterior cruciate ligament or a posterior cruciate ligament of a knee joint which is to be performed under an arthroscope, includes: inserting the arthroscope and a treating portion of an ultrasonic device into a knee joint cavity; bringing the treating portion of the ultrasonic device into contact with a start region to which the anterior cruciate ligament or the posterior cruciate ligament of a femur adheres, and excising the femur and a remaining ligament of the anterior cruciate ligament, or the femur and a remaining ligament of the posterior cruciate ligament by ultrasonically vibrating the treating portion, thereby exposing a footprint region of the femur; and bringing the treating portion of the ultrasonic device into contact with an end region to which the anterior cruciate ligament or the posterior cruciate ligament of a tibia adheres, and excising the tibia and a remaining ligament of the anterior cruciate ligament, or the tibia and a remaining ligament of the posterior cruciate ligament by ultrasonically vibrating the treating portion, thereby exposing a footprint region of the tibia.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 12A is a schematic view showing a state where the ultrasonic vibration is transmitted to the treating portion of the ultrasonic treatment device to dissect the anterior cruciate ligament of a tibia side of the knee joint under the arthroscope;

FIG. 12B is a schematic view showing a state where the ultrasonic vibration is transmitted to the treating portion of the ultrasonic treatment device to dissect the anterior cruciate ligament of the tibia side of the knee joint under the arthroscope, thereby exposing the footprint region (the region to which the anterior cruciate ligament is attached);

FIG. 12C is a schematic view showing a state where a concave hole (a concave region) is formed from the footprint region toward a medial side of a rough surface of the tibia with the treating portion of the ultrasonic treatment device from which the ultrasonic vibration is transmitted to the footprint region of the anterior cruciate ligament of the tibia side of the knee joint under the arthroscope;

DETAILED DESCRIPTION OF THE INVENTION

Embodiments of this invention will be described with reference to the drawings.

Figure 1:
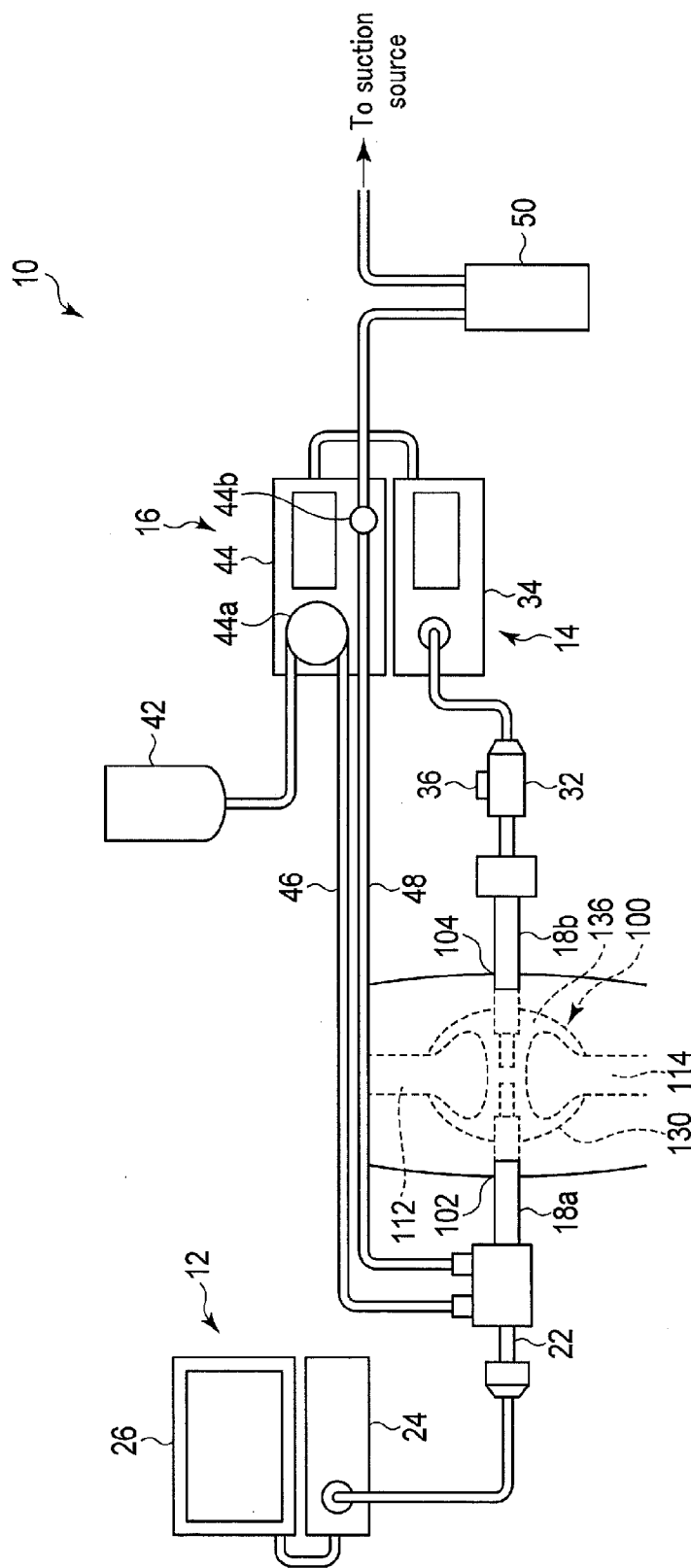
FIG. 1 is a schematic view showing a treatment system for use in a surgical treatment of a knee joint.

When a knee joint 100 is treated, for example, a treatment system 10 shown in FIG. 1 is used. The treatment system 10 has an arthroscope device 12, a treatment device 14, and a perfusion device 16.

The arthroscope device 12 includes an arthroscope 22 to observe an inner part of the knee joint 100, i.e., the inside of a joint cavity 136 of a patient, an arthroscope controller 24 that performs image processing on the basis of a subject image imaged by the arthroscope 22, and a monitor 26 that displays the image generated by the image processing in the arthroscope controller 24. The arthroscope 22 is inserted into the joint cavity 136 of the knee joint 100 through a first cannula 18a that forms a lateral portal 102 via which the inner part of the knee joint 100 of the patient communicates with an outer side of skin. It is to be noted that a position of the portal 102 is not uniform but is suitably determined in accordance with a patient's condition.

The treatment device 14 has an ultrasonic treatment device 32, a treatment device controller 34, and a switch 36. Here, the treatment device controller 34 supplies energy to the ultrasonic treatment device 32 in accordance with an operation of the switch 36 to transmit an ultrasonic vibration to a treating portion 68 of an after-mentioned probe 66 of the ultrasonic treatment device 32. The treatment device 32 is inserted into the joint cavity 136 of the knee joint 100 through a second cannula 18b that forms a medial portal 104 via which the inner part of the joint 100 of the patient communicates with the outer side of the skin. It is to be noted that a position of the portal 104 is not uniform but is suitably determined in accordance with the patient's condition. The switch 36 maintains, for example, a driven state of an ultrasonic transducer in a state where the switch is pressed to be operated, and when the pressed state is released, the driven state of the ultrasonic transducer is released.

Here, it is described that the one switch 36 is disposed, but the switches may be disposed. An amplitude of the ultrasonic transducer can suitably be set by the treatment device controller 34. In consequence, by the operation of the switch 36, a frequency of the ultrasonic vibration to be output from the after-mentioned ultrasonic transducer is the same, but the amplitude may be different. Therefore, the switch 36 can suitably switch the amplitude of the ultrasonic transducer to states such as two large and small states. For example, when the amplitude can be switched to the two large and small states, the ultrasonic vibration of the small amplitude is for use in treating comparatively soft tissues such as a synovial membrane 134, cartilages 112a, 114a and 118a, and meniscuses 142 and 144 shown in FIG. 3 to FIG. 5. The ultrasonic vibration of the large amplitude is for use in treating comparatively hard tissues such as bones (a femur 112, a tibia 114 and a patella 118) shown in FIG. 3 and FIG. 4.

It is to be noted that, for example, the two switches 36 may be disposed in parallel, or a hand switch and a foot switch may selectively be used. Additionally, when the one switch 36 is switched to be used, the ultrasonic vibration of the small amplitude may be output by one operation, and the ultrasonic vibration of the large amplitude may be output by two quick pressing operations as in a double click operation of a mouse for a computer.

The perfusion device 16 includes a bag-shaped liquid source 42 that contains a perfusion liquid such as physiological saline, a perfusion pump unit 44, a liquid supply tube 46 whose one end is connected to the liquid source 42, a liquid discharge tube 48, and a suction bottle 50 connected to one end of the liquid discharge tube 48. The suction bottle 50 is connected to a suction source attached to a wall of an operating room. In the perfusion pump unit 44, the perfusion liquid can be supplied from the liquid source 42 by a liquid supply pump 44a. Additionally, in the perfusion pump unit 44, suction/suction stop of the perfusion liquid in the joint cavity 136 of the knee joint 100 to the suction bottle 50 can be switched by opening/closing a pinching valve 44b as a liquid discharge valve.

The other end of the liquid supply tube 46 that is a liquid supply tube path is connected to the first cannula 18a. In consequence, the perfusion liquid can be supplied into the joint cavity 136 of the knee joint 100 via the first cannula 18a. The other end of the liquid discharge tube 48 that is a liquid discharge tube path is connected to the first cannula 18a. In consequence, the perfusion liquid can be discharged from the joint cavity 136 of the knee joint 100 via the first cannula 18a. It is to be noted that, needless to say, the other end of the liquid discharge tube 48 may be connected to the second cannula 18b, so that the perfusion liquid can be discharged from the knee joint 100.

It is to be noted that, here, the perfusion liquid can be supplied and discharged through the first cannula 18a, but a function that is capable of supplying and/or discharging the perfusion liquid may be imparted to, for example, the arthroscope 22. Similarly, the function that is capable of supplying and/or discharging the perfusion liquid may be imparted to the ultrasonic treatment device 32. In addition, a function that is capable of supplying and discharging the perfusion liquid through the second cannula 18b may be imparted. Furthermore, the perfusion liquid may be supplied and discharged through separate portals.

Figure 2:
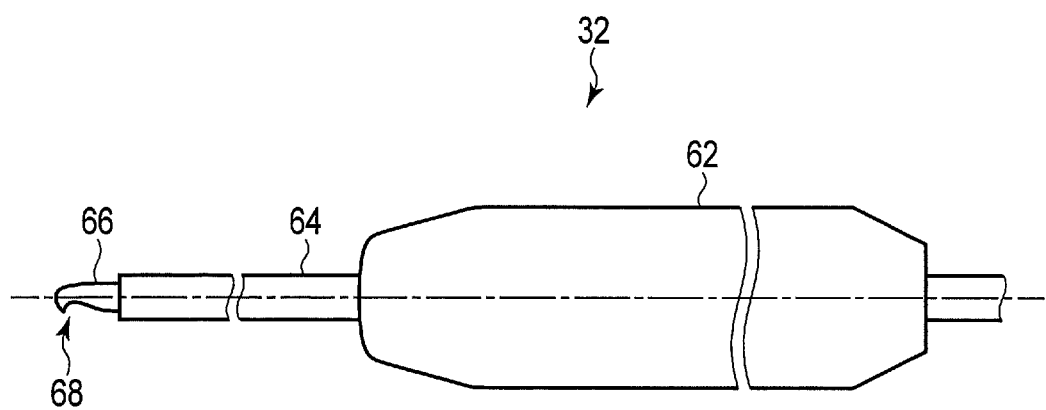
FIG. 2 is a schematic view showing one example of an ultrasonic treatment device (an ultrasonic device) of the treatment system for use in the surgical treatment of the knee joint.

As shown in FIG. 2, the ultrasonic treatment device 32 includes a housing 62, a sheath 64 projected from the housing 62, and the probe 66 inserted into the sheath 64. In particular, outer peripheral surfaces of the housing 62 and the sheath 64 have insulating properties. The probe 66 is made of a metal material such as a titan alloy material capable of transmitting the ultrasonic vibration. To a proximal end of the probe 66, there is fixed an unshown ultrasonic transducer unit disposed in the housing 62. In the ultrasonic treatment device 32, the treating portion 68 of the probe 66 inserted into the sheath 64 is disposed together with the sheath 64 in the joint cavity 136 through the second cannula 18b. Further, when the switch 36 is pressed, energy is supplied from the treatment device controller 34 to the ultrasonic transducer unit fixed to the proximal end of the probe 66, and the ultrasonic transducer ultrasonically vibrates. This vibration is transmitted from the proximal end of the probe 66 toward a distal end side, and hence with the aid of the treating portion 68 of a distal end of the probe 66, the hard tissue (the bone tissue or the like) can be resected and the soft tissue (the cartilage, a membrane tissue or the like) can be excised.

It is to be noted that a shape of the treating portion 68 can suitably be selected in accordance with a treatment region. Here, there is described an example where a hook type of treating portion shown in FIG. 2 is used, but various shapes such as a rake type, a blade type and a curette type can selectively be used in consideration of an accessibility to the treatment region, an adaptability to the treatment on the basis of a position, a shape, a size or the like of a blade portion of the treating portion 68, or the like.

A structure of the knee joint 100 will briefly be described. Hereinafter, the knee joint 100 of a right knee will be described as an example.

Figure 3:
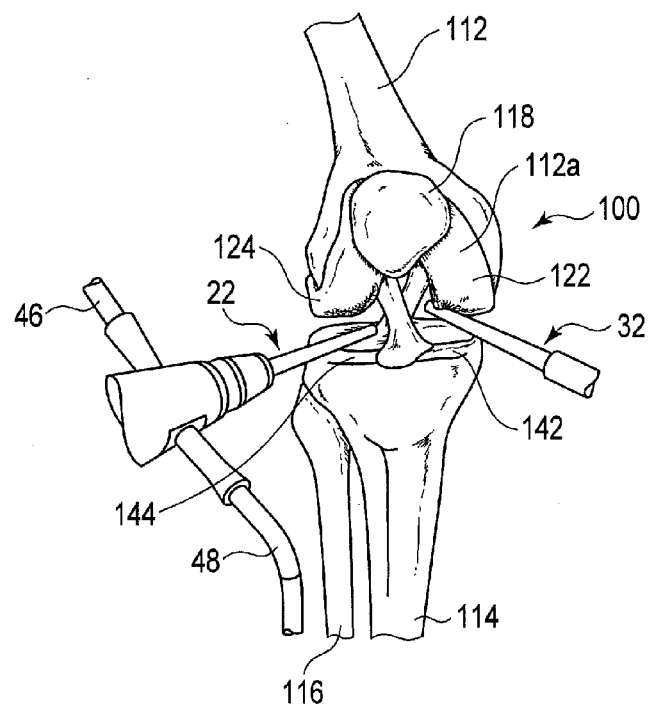
FIG. 3 is a schematic view showing a state where an arthroscope and a treating portion of the ultrasonic treatment device are inserted from separate portals, respectively, to an articular capsule of the knee joint of a right knee seen from the anterior side.
Figure 4:
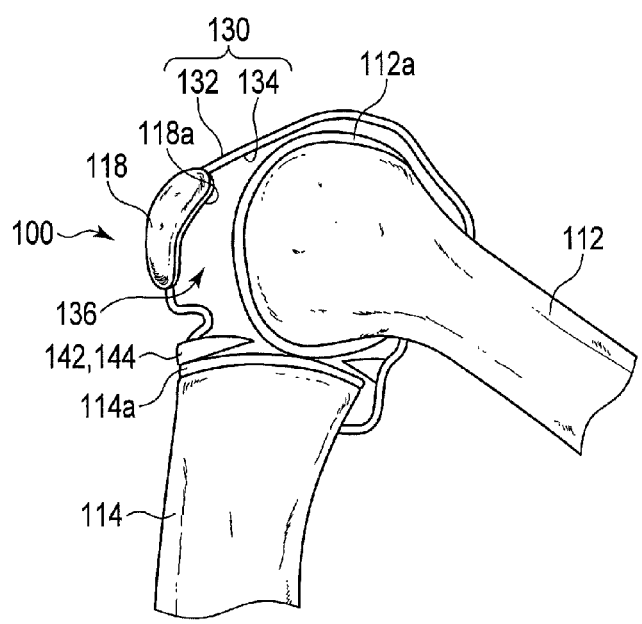
FIG. 4 is a schematic side view showing a state where the knee joint of the right knee encapsulated in the articular capsule is seen from the medial side.

As shown in FIG. 3, the knee joint 100 is mainly constituted of a femur 112, a tibia 114, a fibula 116, and a patella 118. As shown in FIG. 4, the knee joint 100 is encapsulated in a joint capsule 130. The joint capsule 130 includes a fibrous tunica 132 on a lateral side and the synovial membrane 134 on a medial side. The synovial membrane 134 forms pleats and secretes a synovial fluid, and hence the knee joint 100 smoothly moves. The inside of the joint capsule 130 is called the joint cavity 136. The joint cavity 136 is filled with the synovial fluid to be secreted from the synovial membrane 134. The joint cavity 136 of the knee joint 100 is incompletely divided into four cavities (a suprapatellar bursa, a patellofemoral joint cavity, a lateral femorotibial joint cavity and a medial femorotibial joint cavity), and the synovial membrane pleat is present as a partition wall between these cavities.

Additionally, in the knee joint 100, each of the cartilages (joint cartilages) 112a, 114a and 118a is present between the bones (the femur 112, the tibia 114 and the patella 118). By the cartilages 112a, 114a and 118a, impact can be absorbed in the knee joint 100, and the knee joint 100 can smoothly move.

As shown in FIG. 3, surfaces of the femur 112 which are joined to the tibia 114 are referred to as a medial condyle 122 and a lateral condyle 124, respectively. In a superior surface of the tibia 114, there are two surfaces to be joined to the medial condyle 122 and the lateral condyle 124 of the femur 112. Between the medial condyle 122 and the lateral condyle 124 of the femur 112 and the upper surface of the tibia 114, the meniscuses 142 and 144 and ligaments 152 and 154 adhere.

Figure 5:
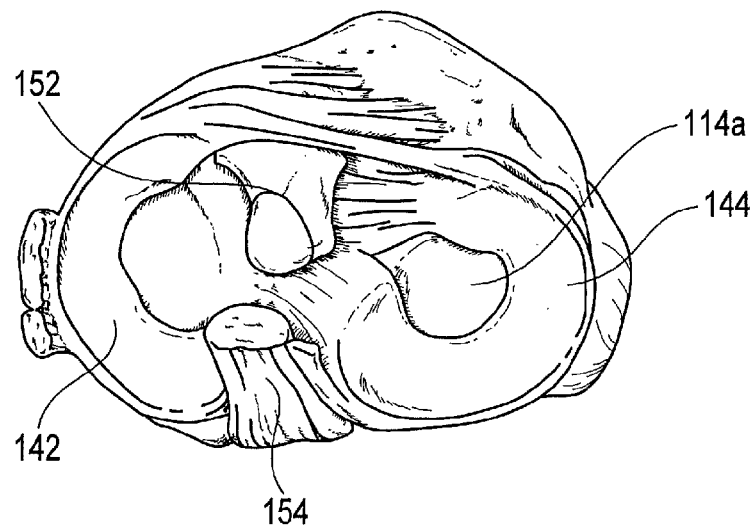
FIG. 5 is a schematic view showing a state where a medial meniscus, a lateral meniscus, an anterior cruciate ligament and a posterior cruciate ligament of the knee joint of the right knee are seen from the superior side.

As shown in FIG. 5, the meniscuses 142 and 144 form a pair on lateral and medial sides. A superior surface of the medial meniscus 142 extends along the spherical cartilage 112a disposed in the medial condyle 122 of the femur 112, and an inferior surface of the medial meniscus extends along the flat cartilage 114a disposed on the superior surface of the tibia 114. Similarly, a superior surface of the lateral meniscus 144 extends along the spherical cartilage 112a disposed in the lateral condyle 124 of the femur 112, and an inferior surface of the lateral meniscus extends along the flat cartilage 114a disposed on the superior surface of the tibia 114. Consequently, the meniscuses 142 and 144 are formed so that lateral edge portions of the meniscuses are thick and medial edge portions of the meniscuses are thin. It is to be noted that the lateral edge portions of the medial meniscus 142 and the lateral meniscus 144 are linked to the joint capsule 130.

In the knee joint 100, an anterior cruciate ligament 152 and a posterior cruciate ligament 154 are present. When the knee joint 100 is seen from an anterior side, the anterior cruciate ligament 152 is present in the anterior side and the posterior cruciate ligament 154 is present in a posterior side. One end of the anterior cruciate ligament 152 is passed through a space between the medial condyle 122 and the lateral condyle 124 of the femur 112 and fixed to the posterior side of the femur, and the other end of the anterior cruciate ligament is fixed to the anterior side of the superior surface of the tibia 114. The anterior cruciate ligament 152 has its start region in a medial surface posterior region of the lateral condyle 124 of the femur 112, and adheres to an anterior intercondylar fossa area (an end region) of the tibia 114. One end of the posterior cruciate ligament 154 is fixed to a slightly anterior region of the femur 112, and the other end of the posterior cruciate ligament is fixed to the posterior side of the superior surface of the tibia 114. The posterior cruciate ligament 154 has its start region in a lateral surface anterior region of the medial condyle 122 of the femur 112, and adheres to a posterior intercondylar fossa area (an end region) of the tibia 114.

Next, there will be described a method in which a surgeon (an operator) uses the treatment system 10 mentioned above to excise a damaged region of the meniscus 142 or 144 under the arthroscope 22 to the patient who has the damaged region in at least one of the meniscuses 142 and 144 present between the femur 112 and the tibia 114 of the knee joint 100.

Figure 6:
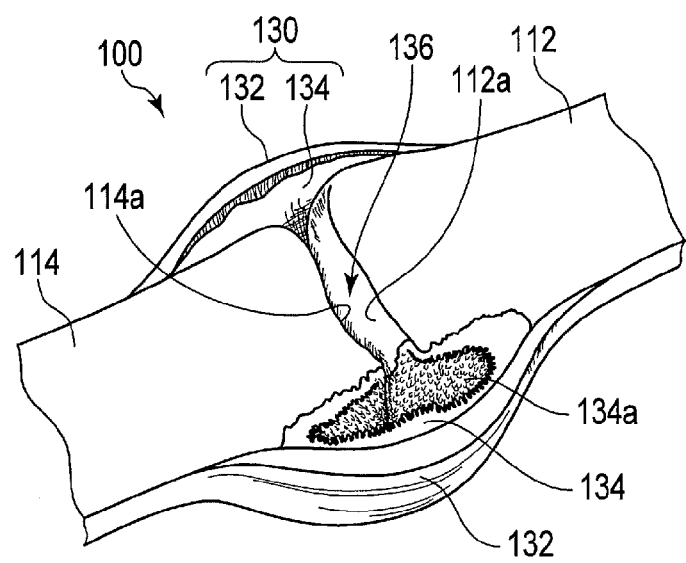
FIG. 6 is a schematic coronary cross-sectional view schematically showing a state where there is inflammation of a synovial membrane in the articular capsule of the knee joint.

As to the damage of the meniscus 142 or 144 of the knee joint 100, in general, there are a case where the meniscus is damaged due to an external injury or the like and a case where the meniscus is damaged due to repeatedly loaded stress. As to the meniscus 142 or 144, the damages are mainly and often caused to an anterior horn of the medial meniscus 142 or posterior regions (posterior horns or posterior nodes) of the medial meniscus 142 and the lateral meniscus 144. In addition, when the meniscus 142 or 144 is damaged, as shown in FIG. 6, such inflammation as shown by a reference sign 134a might be caused to the meniscus together with the synovial membrane 134.

A condition of the knee joint 100 is confirmed by use of an X-ray, MRI or the like. When the damage is confirmed in the meniscus 142 or 144, a damaged condition of the meniscus 142 or 144 is confirmed in advance.

There are prepared an instrument to form the portals 102 and 104 in the knee joint 100, and an instrument for use in a surgical treatment of excising an inflamed region of the synovial membrane 134 and damaged regions of the meniscuses 142 and 144. It is to be noted that the treating portion 68 of the ultrasonic treatment device 32 is formed into a suitable shape such as the hook type.

The surgeon forms the first portal 102 on anterior and lateral side of the knee joint to the patient who bends the knee joint 100 of the right knee. When necessary, the first cannula 18a is disposed in the portal 102. A distal end of the arthroscope 22 is disposed in the joint cavity 136 of the knee joint 100 through the first cannula 18a. Here, the first cannula 18a is not necessarily required, when the perfusion device 16 is connectable to the arthroscope 22.

The joint cavity 136 of the knee joint 100 is filled with saline by use of the perfusion device 16. In this state, the medial side of the joint cavity 136 of the knee joint 100 is suitably observed by using the arthroscope 22. Further, the damaged region of the meniscus 142 or 144 is disposed in a view field of the arthroscope 22 to confirm the damage. In addition, an inflamed condition of the synovial membrane 134 on the medial side of the joint capsule 130 of the knee joint 100 is confirmed.

Figure 7:
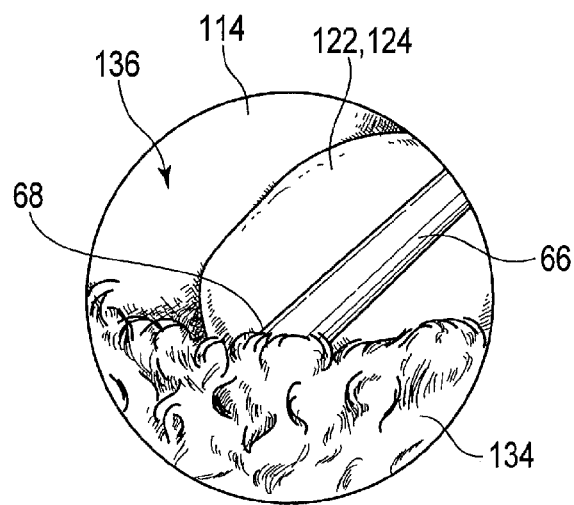
FIG. 7 is a schematic view showing a state where an ultrasonic vibration is transmitted to the treating portion of the ultrasonic treatment device to excise the synovial membrane in the articular capsule of the knee joint under the arthroscope.

The surgeon forms the second portal 104 on the anterior and medial side to the patient who bends the knee joint 100. When necessary, the second cannula 18b is disposed in the portal 104. The treating portion 68 of the ultrasonic treatment device 32 is disposed in the joint cavity 136 of the knee joint 100 through the second cannula 18b. When the inflamed region is present in the synovial membrane 134 of the joint capsule 130 confirmed with the arthroscope 22, as shown in FIG. 7, the surgeon approaches the inflamed region with the treating portion 68 of the ultrasonic treatment device 32 to bring the treating portion into contact with the inflamed region while observing the inflamed region with the arthroscope 22. Further, the surgeon operates the switch 36 of the treatment device 14 to generate the ultrasonic vibration of the suitable amplitude in the ultrasonic transducer, thereby only moving the treating portion 68 in an axial direction of the probe 66, whereby the inflamed region 134a of the synovial membrane 134 and/or an inflamed synovial membrane is excised with the treating portion 68 to which the vibration is transmitted. The excised inflamed region of the synovial membrane 134 is flown with momentum in excising the region. At this time, the surgeon suitably moves the ultrasonic treatment device 32 and also suitably moves the arthroscope 22 to excise the inflamed region 134a of the synovial membrane 134 and/or the inflamed synovial membrane and further a peripheral region with the treating portion 68 of the ultrasonic treatment device 32 while always disposing the treating portion 68 in the view field of the arthroscope 22. In the synovial membrane 134, the excised inflamed region 134a and the peripheral region are discharged to the suction bottle 50 through the first cannula 18a and the liquid discharge tube 48.

A head (a treating portion) of an unshown shaver that has heretofore been used in removing the inflamed region of the synovial membrane 134 or the like has a structure to intertwine the inflamed region by periaxial rotation. Thus, the shaver performs the treatment while intertwining (winding) the inflamed region, and hence there is a high possibility that a peripheral tissue in the knee joint 100 is wound during the treatment. In addition, power is securely transmitted from a motor of the shaver to the head, and hence it is difficult to form a portion between the motor and the head of the shaver into a suitable shape, and additionally, a head portion is formed to be larger than the treating portion 68 of the ultrasonic treatment device 32. In consequence, it is very difficult for the head portion of the shaver to especially access the posterior side of the knee joint 100. Therefore, even by use of the shaver that has heretofore been used, it might be difficult to remove the synovial membrane 134. When the treatment is performed by using the ultrasonic treatment device 32, it is not necessary to rotate the treating portion 68. Therefore, damages due to the winding of the peripheral tissue in the knee joint 100 can be decreased. In addition, when the treatment is performed by using the ultrasonic treatment device 32, the treating portion 68 can be formed into the suitable shape, the treating portion 68 can be formed to be smaller, and the probe 66 can be formed to be thinner, so that a moving range of the treating portion 68 to the second cannula 18b can be increased. Therefore, in a case where the ultrasonic treatment device 32 is used, for example, the posterior side of the knee joint 100 can more easily be accessed as compared with a case where the shaver is used. Consequently, in the case the ultrasonic treatment device 32 is used, the inflamed region of the synovial membrane 134 can more easily be excised than in the case where the shaver is used.

In addition, as described above, the shaver has the structure to intertwine the inflamed regions of the synovial membrane 134 by the periaxial rotation. Consequently, the shaver operates to tear off the synovial membrane 134, and the excised region of the synovial membrane 134 easily bleeds. On the other hand, the treating portion 68 of the ultrasonic treatment device 32 does not periaxially rotate, and the inflamed region can be excised only by moving the treating portion in the axial direction of the probe 66. Further, in the case where the ultrasonic treatment device 32 is used, the excised region is flown unlike the case where the shaver is used, and hence the view field of the arthroscope 22, especially the view field of the treatment region is easily acquired.

Figure 8:
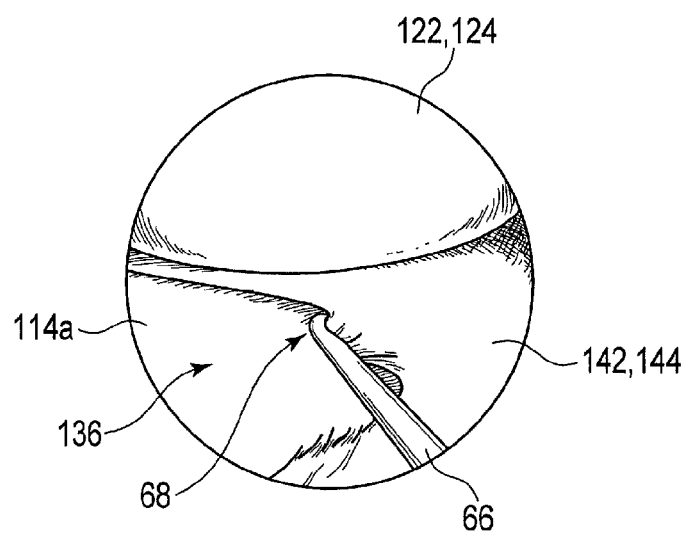
FIG. 8 is a schematic view showing a state where the ultrasonic vibration is transmitted to the treating portion of the ultrasonic treatment device to excise a damaged region of the meniscus of the knee joint under the arthroscope.

As described above, the surgeon removes the inflamed region of the synovial membrane 134 by use of the ultrasonic treatment device 32, and then while moving the arthroscope 22 to confirm the inside of the joint cavity 136 of the knee joint 100, the surgeon moves the ultrasonic' treatment device 32 to dispose the damaged region of the meniscus 142 or 144 in the view field of the arthroscope 22 as shown in FIG. 8. Furthermore, the treating portion 68 of the ultrasonic treatment device 32 is disposed to face the damaged region of the meniscus 142 or 144. That is, here, the treating portion 68 of the ultrasonic treatment device 32 that is the same as the portion used to excise the synovial membrane 134 is disposed as it is to face the damaged region of the meniscus 142 or 144. Therefore, the treating portion 68 approaches treatment regions such as the anterior horn of the medial meniscus 142 and the posterior horns and posterior nodes of the medial meniscus 142 and the lateral meniscus 144 to face them. The treating portion 68 of the ultrasonic treatment device 32 is brought into contact with the treatment region of the meniscus 142 or 144, and the switch 36 is operated to generate the ultrasonic vibration of the suitable amplitude in the ultrasonic transducer. In consequence, the treating portion 68 to which the ultrasonic vibration is transmitted is only moved in the axial direction of the probe 66, to remove the damaged meniscus 142 or 144 in the treatment region. That is, a region of the meniscus 142 or 144 in which tear or damage denaturation occurs is excised with the treating portion 68 to which the ultrasonic vibration is transmitted, to perform dissection. As shown in FIG. 10B, the surgeon can easily form a surface treated by the treating portion 68 of the ultrasonic treatment device 32 to which the ultrasonic vibration is transmitted, as a smooth surface without forming any corner portions in the treatment region of the meniscus 142 or 144 by suitably moving the treating portion 68 in accordance with the movement of the probe 66 in the axial direction. When the treatment object region of the meniscus 142 or 144 is removed, a dented region having a substantially circular vertical cross section is formed, and there are smoothly continued a removed surface from which the treatment object region of the meniscus 142 or 144 is removed and a non-removed surface adjacent to the removed surface. In consequence, the region treated with the treating portion 68 of the ultrasonic treatment device 32 by the surgeon is hard to be stuck on another region.

It is to be noted that, by the operation of the switch 36, the amplitude of the ultrasonic transducer in a case where the synovial membrane 134 is removed may be adjusted to be different from the amplitude of the ultrasonic transducer in a case where the damaged region of the meniscus 142 or 144 is excised.

Figure 9A:
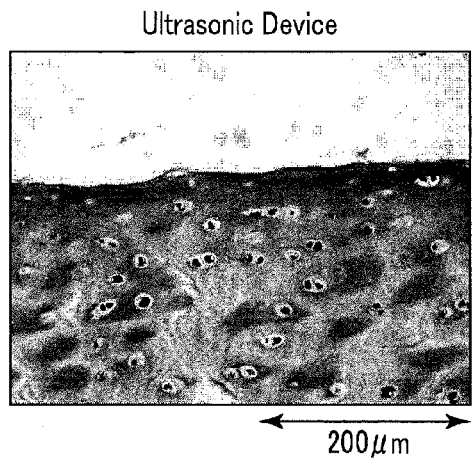
FIG. 9A is a schematic view showing a state where a condition of a cartilage of a joint excised with the treating portion of the ultrasonic treatment device to which the ultrasonic vibration is transmitted is enlarged and observed.

It might be difficult for the unshown shaver head that has heretofore been used in shaving the bone to access the damaged region of the meniscus 142 or 144. The ultrasonic treatment device 32 can be formed into a suitable shape between the proximal end of the probe 66 and the treating portion 68 of the distal end, the treating portion 68 can be formed to be small, and hence the ultrasonic treatment device can more easily have access toward the posterior side of the knee joint 100 than the shaver. Consequently, in the case where the treatment is performed by using the ultrasonic treatment device 32, the damaged region of the meniscus 142 or 144 can more easily be excised than in the case where the shaver is used. Additionally, as shown in FIG. 9A, the surface treated by the ultrasonic treatment device 32 can smoothly be formed by, for example, a blade surface of the hook-shaped treating portion 68. On the other hand, the shaver shaves the surface by the rotation of the head, and hence it is more difficult to smoothen the cut-off surface than in the case where the ultrasonic treatment device 32 is used.

Figure 9B:
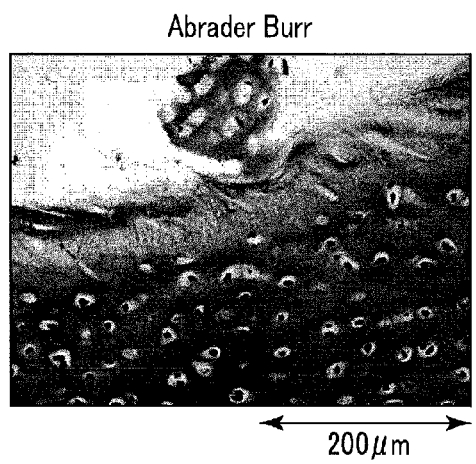
FIG. 9B is a schematic view showing a state where a condition of the cartilage of the joint abraded with an abrader burr is enlarged and observed.

It is to be noted that when an abrader burr is used in the treatment of a soft tissue such as the meniscus 142 or 144, the treated surface (an abraded surface) is disadvantageously made fluffy as shown in FIG. 9B. Consequently, in the case where the abrader burr is used, it is more difficult to smoothen the surface and it is easier to generate concave and convex areas in the excised region than in the case where the ultrasonic treatment device 32 is used. As shown in FIG. 9A and FIG. 9B, in the case where the treating portion 68 of the ultrasonic treatment device 32 is used, the treated surface is more easily formed precisely and smoothly than in the case where the abrader burr is used. Therefore, in the case where the ultrasonic treatment device 32 is used, the concave and convex areas of the excised region can be decreased as compared with the case where the abrader burr is used.

Thus, the ultrasonic treatment device 32 is used, and hence the device can smoothly be moved between the treatment region of the meniscus 142 or 144 and the femur 112 and between the treatment region of the meniscus 142 or 144 and the tibia 114. Therefore, the treatment in which the ultrasonic treatment device 32 is used contributes to a smooth joint movement in which sticking of the femur 112 to the meniscus 142 or 144 that remains to be excised and sticking of the tibia 114 to the meniscus 142 or 144 that remains to be excised are eliminated.

As described above, the surgeon performs the treatment of the damaged region of the meniscus 142 or 144 to the patient. Afterward, the surgeon pulls out the treating portion 68 of the ultrasonic treatment device 32 from the second cannula 18b and pulls out the distal end of the arthroscope 22 from the first cannula 18a. Furthermore, the first and second cannulas 18a and 18b are removed from the knee joint 100. Further, the portals 102 and 104 are sutured.

As described above, the technique of excising the damaged region of the meniscus 142 or 144 under the arthroscope 22 can be considered as follows.

By use of the treatment system 10, the surgeon can perform a series of treatment of excising the synovial membrane 134 and excising the damaged region of the meniscus 142 or 144 with the treating portion 68 of the ultrasonic treatment device 32 while the one ultrasonic treatment device 32 is disposed as it is in the second cannula 18b. Consequently, during the surgical treatment, the surgeon does not need to replace the treatment device 32 disposed in the joint cavity 136, and hence surgical treatment time can be shortened.

The probe 66 of the ultrasonic treatment device 32 can be formed into the suitable shape, and the treating portion 68 can be formed to be smaller than the shaver or the abrader burr. Consequently, in the treatment in which the ultrasonic treatment device 32 is used, a movable range to the second cannula 18b can be increased, and treatment regions such as the anterior horn of the medial meniscus 142 and the posterior horns and posterior nodes of the medial meniscus 142 and the lateral meniscus 144 can more easily be approached as compared with the case where the shaver is used. Additionally, in the treatment of the ultrasonic treatment device 32, the more precise and smoother treated surface can be formed than in the case where the shaver or the abrader burr is used. Consequently, for example, when the surgeon performs the treatment by use of the ultrasonic treatment device 32 and then the patient bends and stretches the knee joint 100 to move the meniscus 142 or 144, the meniscus can be prevented from being stuck on the femur 112 or the tibia 114, which can contribute to the smooth joint movement.

Figure 9C:
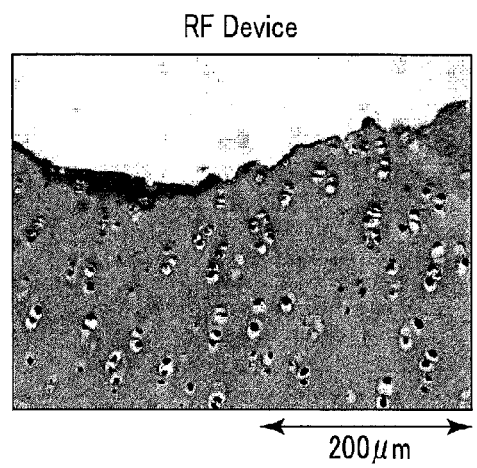
FIG. 9C is a schematic view showing a state where a condition of the cartilage of the joint excised with an RF device is enlarged and observed.

In addition, the surgeon uses the ultrasonic treatment device 32 and hence does not have to use a high frequency device (an RF device). As shown in FIG. 9C, when the treatment is performed by using the high frequency device, there is the fear that the surface (an inferior bone of the cartilage) is invaded by heat. On the other hand, as shown in FIG. 9A, in the case where the ultrasonic treatment device 32 is used, for example, the cartilage 114a of the tibia 114 under the meniscus 142 or 144 is less invaded by heat, and thermal necrosis is prevented from being caused to the cartilage 114a in the treated surface excised by the treating portion 68, as compared with the case where the high frequency device is used.

Next, there will be described a method in which the surgeon uses the treatment system 10 mentioned above to perform a surgical treatment of excising a damaged region of the cartilage 112a under the arthroscope 22 to the patient who has the damaged region in the spherical cartilage 112a. Here, together with the removal of the synovial membrane 134 and the treatment of the damaged region of the meniscus 142 or 144, there is described a method of removing a denatured cartilage in a case where osteochondritis dissecans (OCD) occur.

The knee joint 100 might cause the osteochondritis dissecans. The surgeon confirms the osteochondritis dissecans by use of MRI or the like. Degrees of progress of the osteochondritis dissecans are indicated as, for example, grades of ICRS (International Cartilage Repair Society), i.e., Grade 0 (Normal), Grade 1 (Stable, continuity: Softened area covered by intact cartilage), Grade 2 (Partial discontinuity, stable on probing), Grade 3 (Complete discontinuity, "dead in situ", not dislocated), Grade 4 (Dislocated fragment, loose within the bed or empty defect. >10 mm in depth is B-subgroup). In the knee joint 100, the cartilages 112a are damaged in, for example, the medial condyle 122 and the lateral condyle 124 of the femur 112 due to the osteochondritis dissecans.

There are prepared the instrument to form the portals 102 and 104 in the knee joint 100, and an instrument for use in a surgical treatment of excising the cartilage and the bone. It is to be noted that the treating portion 68 of the ultrasonic treatment device 32 is formed into the suitable shape, e.g., the hook type.

The surgeon disposes the distal end of the arthroscope 22 in the joint cavity 136 of the knee joint 100 of the patient through the first cannula 18a. The surgeon fills the joint cavity 136 of the knee joint 100 of the patient with the saline (the perfusion liquid) by use of the perfusion device 16. In this state, the surgeon suitably observes the inside of the joint cavity 136 of the knee joint 100 of the right knee by use of the arthroscope 22. Further, the surgeon disposes the damaged region of the meniscus 142 or 144 in the view field of the arthroscope 22 to confirm the damage. Additionally, the surgeon confirms the inflammation of the synovial membrane 134 in the joint capsule 130 of the knee joint 100.

The surgeon disposes the treating portion 68 of the ultrasonic treatment device 32 in the joint cavity 136 of the knee joint 100 of the patient through the second cannula 18b. In a case where a region that causes inflammation is present in the synovial membrane 134 of the joint capsule 130 confirmed with the arthroscope 22, the surgeon excises the inflamed region from the synovial membrane 134 with the treating portion 68 of the ultrasonic treatment device 32 to which the ultrasonic vibration is transmitted, while observing the inflamed region with the arthroscope 22. Similarly, the ultrasonic vibration is transmitted to the same treating portion 68 of the ultrasonic treatment device 32 to excise the damaged region of the meniscus 142 or 144. That is, when necessary, the inflamed region of the synovial membrane 134 or the damaged region of the meniscus 142 or 144 is excised as described above, or when possible, the damaged region of the meniscus 142 or 144 is sutured and treated.

For example, when the cartilage 112a attached to the medial condyle 122 of the femur 112 is damaged, the surgeon confirms the grade of the osteochondritis dissecans with the arthroscope 22. By use of the arthroscope 22, the surgeon confirms whether a part of the cartilage 112a is softened (Grade 1), whether laceration such as partial tear is present in a part of the cartilage 112a (Grade 2), whether a part of the cartilage 112a is discontinued from a bone (the medial condyle 122 of the femur 112) to which the cartilage 112a adheres (Grade 3), or whether a bone cartilage piece is liberated and the bone (the medial condyle 122 of the femur 112) to be hidden behind the cartilage 112a is exposed (Grade 4), to judge the grade. Additionally, in each of Grades 1 to 4, presence/absence of the bone spurs and presence/absence of hardened regions are confirmed to the medial condyle 122 and the lateral condyle 124 of the femur 112.

Figure 10A:
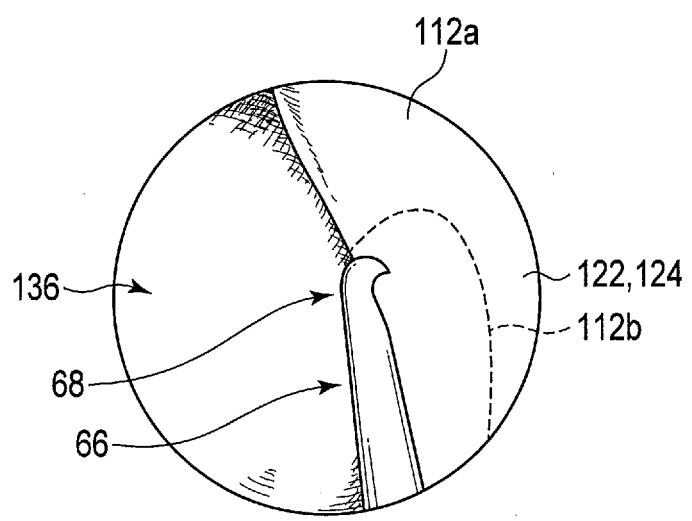
FIG. 10A is a schematic view showing a state where the ultrasonic vibration is transmitted to the treating portion of the ultrasonic treatment device to remove a treatment object region of the cartilage of the knee joint under the arthroscope.
Figure 10B:
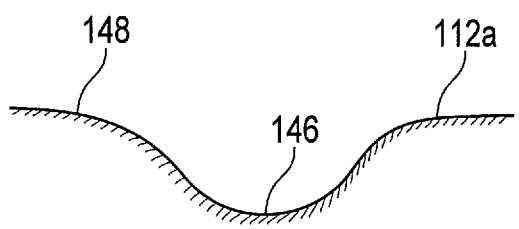
FIG. 10B is a schematic view showing a condition where of a treated surface formed by the treating portion of the ultrasonic treatment device when the ultrasonic vibration is transmitted to the treating portion of the ultrasonic treatment device to remove the treatment object region of the cartilage of the knee joint under the arthroscope.

Further, as shown in FIG. 10A, the treating portion 68 of the ultrasonic treatment device 32 is brought into contact with the treatment object region of the cartilage 112a while observing the treatment object region always disposed in the view field of the arthroscope 22. In this state, the switch 36 is operated to suitably perform the treatment to the treatment object region by use of the ultrasonic vibration. At this time, as shown in FIG. 10B, the surgeon can easily form the treated surface by the treating portion 68 to which the ultrasonic vibration of the ultrasonic treatment device 32 is transmitted, as the smooth surface without forming any corner portions therein, by suitably moving the treating portion 68 in accordance with the movement of the probe 66 in the axial direction. As shown in FIG. 10B, when the treatment object region of the cartilage 112a is removed, a dented region having a substantially circular vertical cross section is formed, and there are smoothly continued the removed surface from which the treatment object region of the cartilage 112a is removed and the non-removed surface adjacent to the removed surface. In consequence, the region treated with the treating portion 68 of the ultrasonic treatment device 32 by the surgeon is hard to be stuck on another region.

Here, as shown in FIG. 10B, the treatment is performed without leaving any corner portions in treated regions of the cartilage 112a when the surgeon judges as one of Grade 2 to Grade 4, as well as the softened region 112b of the cartilage 112a is removed.

When the surgeon judges that a condition of a part of the cartilage 112a is Grade 2, as shown in FIG. 10A, the treating portion 68 of the ultrasonic treatment device 32 is faced to a torn region (a treatment object region) 112b of the cartilage 112a. Further, the torn region of the cartilage 112a is removed by moving the treating portion 68 along the axial direction of the probe 66 while transmitting the ultrasonic vibration to the treating portion 68 of the ultrasonic treatment device 32. In addition, the bone spur formed in Grade 2 is removed by transmitting the ultrasonic vibration to the treating portion 68 of the ultrasonic treatment device 32. Also at this time, the treatment is performed without leaving any corner portions in treated regions of the cartilage 112a and the medial condyle 122 of the femur 112.

When the surgeon judges that the condition of a part of the cartilage 112a is Grade 3, as shown in FIG. 10A, the treating portion 68 of the ultrasonic treatment device 32 is faced to the torn region (the treatment object region) 112b of the cartilage 112a and a torn region of the medial condyle 122 of the femur 112. Further, the torn region 112b of the cartilage 112a and the torn region of the medial condyle 122 of the femur 112 are removed together with the osteophyte formed in the medial condyle 122 of the femur 112 and the like, by moving the treating portion 68 along the axial direction of the probe 66 while transmitting the ultrasonic vibration to the treating portion 68 of the ultrasonic treatment device 32. Also at this time, the treatment is performed without leaving any corner portions in the treated regions of the cartilage 112a and the medial condyle 122 of the femur 112.

When the surgeon judges that the condition of a part of the cartilage 112a is Grade 4, the torn region (the treatment object region) 112b of the cartilage 112a shown in FIG. 10A might peel from the medial condyle 122 of the femur 112. In this case, when the inferior bone (the medial condyle 122 of the femur 112) of the cartilage 112a undergoes necrosis due to an interruption in circulation of blood or the like, the bone cartilage piece separates to be liberated as a loose body in the joint capsule 130. In addition, the loose body might be separated also from the cartilage 112a into the joint capsule 130. In such a case, the treating portion 68 of the ultrasonic treatment device 32 is faced to the torn region 112b of the cartilage 112a and the torn region of the medial condyle 122 of the femur 112. Further, the torn region 112b of the cartilage 112a and the torn region of the medial condyle 122 of the femur 112 are removed together with the bone spur formed in the medial condyle 122 of the femur 112, by moving the treating portion 68 along the axial direction of the probe 66 while transmitting the ultrasonic vibration to the treating portion 68 of the ultrasonic treatment device 32. Also at this time, the treatment is performed without leaving any corner portions in the treated regions of the cartilage 112a and the medial condyle 122 of the femur 112. It is to be noted that the region liberated from the cartilage 112a is sucked or curetted to be removed. Further, excision of the deformed cartilage 112a, removal of the curetted or liberated cartilage piece, and grafting of the cartilage 112a are carried out. For example, when the bone cartilage piece is grafted, a region to be grafted needs to be dissected. In this case, the ultrasonic vibration is transmitted to the treating portion 68 of the ultrasonic treatment device 32 to smoothly continue the removed surface and the non-removed surface adjacent to the removed surface as shown in FIG. 10B, thereby carrying out the dissection. Further, the bone cartilage piece is fixed by a known method.

Thus, in accordance with the condition, the treating portion 68 is moved along the axial direction of the probe 66 while transmitting the ultrasonic vibration to the treating portion 68 of the ultrasonic treatment device 32, to suitably dissect the cartilage 112a. In addition, the ultrasonic vibration is transmitted to the treating portion 68 of the same ultrasonic treatment device 32, to remove the bone spur. Also when the bone spur is removed, the treatment is performed without leaving any corner portions and the smooth surface is formed without forming any corner portions in the same manner as shown in FIG. 10B.

Here, there has been described the example where the cartilage 112a of the femur 112 and the femur 112 are treated, but the inferior cartilage 118a (see FIG. 4) of the patella 118 in chondromalacia patellae can similarly be treated.

As described above, the technique of removing the damaged region 112b of the cartilage 112a under the arthroscope 22 can be considered as follows.

By use of the treatment system 10, the surgeon can perform a series of treatment of removing the cartilage 112a and the treatment object region of the femur 112 with the treating portion 68 of the treatment device 32 while the one ultrasonic treatment device 32 is disposed as it is in the second cannula 18b. Consequently, by use of the treatment system 10, the surgeon can perform a series of treatment of excising the synovial membrane 134, excising the damaged region of the meniscus 142 or 144 and removing the cartilage 112a and the treatment object region of the femur 112 with the treating portion 68 of the treatment device 32 while the one ultrasonic treatment device 32 is disposed as it is in the second cannula 18b.

Further, the surgeon has heretofore replaced and used different instruments to the portal 104 by, for example, using the shaver or the like in a smoothening treatment of the cartilage 112a and using the abrader burr or the like in the smoothening treatment of the femur 112, the tibia 114 or the patella 118. When the cartilage 112a and the treatment object region 112b of the femur 112 are removed, the ultrasonic treatment device 32 does not have to be replaced to the portal 104. These treatments can be performed with the one ultrasonic treatment device 32. Consequently, during the surgical treatment, the surgeon does not have to replace the treatment device 32 disposed in the joint cavity 136, and hence the surgical treatment time can be shortened.

The probe 66 of the ultrasonic treatment device 32 can be formed into the suitable shape, and the treating portion 68 can be formed to be smaller than the shaver or the abrader burr. Consequently, in the treatment in which the ultrasonic treatment device 32 is used, the movable range to the cannula 18b can be increased, and treatment regions such as back surfaces or the like of the medial condyle 122 and the lateral condyle 124 of the femur 112 and a treatment region of a joint surface (an inferior surface) of the patella 118 can more easily be approached as compared with the case where the shaver or the abrader burr is used. Additionally, in the treatment of the ultrasonic treatment device 32, the more precise and smoother treated surface can be formed than in the case where the shaver or the abrader burr is used. Consequently, for example, when the surgeon performs the treatment by use of the ultrasonic treatment device 32 and then the patient bends and stretches the knee joint 100 to move the femur 112, the tibia 114 and the patella 118, the femur 112, the tibia 114 and the patella 118 can be prevented from being stuck on one another, which can contribute to the smooth joint movement.

The abrader burr abrades the bone (the bone spur) that is the hard tissue by the periaxial rotation, and hence loads that act on the abrader burr increase in a case where the bone is abraded. Consequently, the abrader burr might noticeably entirely be vibrated by the loads onto the treating portion. On the other hand, the treating portion 68 of the ultrasonic treatment device 32 is not periaxially rotated but the bone can be resected only by moving (vibrating) the treating portion in the axial direction of the probe 66. Consequently, loads that act on the housing 62 or the like through the treating portion 68 are small in a case where the bone is resected by the treating portion 68. In consequence, the ultrasonic treatment device 32 inserted into the joint cavity 136 of the knee joint 100 through the portal 104 does not noticeably vibrate. That is, in the case where the bone is resected by the treating portion 68, leaping of the treating portion 68 is not caused by a rotary motion as in the abrader burr, and hence damages of the peripheral tissue can be decreased.

In addition, the surgeon uses the ultrasonic treatment device 32 and hence does not have to use the high frequency device. When the treatment is performed by using the high frequency device, there is the fear that the surface is invaded by heat. On the other hand, when the ultrasonic treatment device 32 is used, normal regions of the cartilages 112a, 114a and 118a of the femur 112, the tibia 114 and the patella 118 are less invaded by heat, and the thermal necrosis is prevented from being caused to the cartilages 112a, 114a and 118a.

Next, there will be described a method in which the surgeon uses the treatment system 10 mentioned above to excise the anterior cruciate ligament 152 under the arthroscope 22 to the patient who has the damaged region in the anterior cruciate ligament 152, and a reconstructing method of the anterior cruciate ligament 152. Additionally, here, there are treated the inflammation of the synovial membrane 134, the damaged region of the meniscus 142 or 144 and the osteochondritis dissecans (OCD) which often occur together with the damage of the anterior cruciate ligament 152.

There are prepared an instrument to form the portals 102 and 104 in the knee joint 100, and an instrument for use in a surgical treatment of reconstructing the anterior cruciate ligament 152. It is to be noted that the treating portion 68 of the ultrasonic treatment device 32 is formed into a suitable shape such as the hook type.

When the anterior cruciate ligament 152 is reconstructed, the surgeon first collects a tendon to be implanted from a hamstring (a semitendinosus muscle, or a gracilis muscle), a patellar tendon or the like and prepares a graft 156 (see FIG. 14) that replaces the anterior cruciate ligament 152. The surgeon judges a position of the patient from which the tendon to be implanted is to be collected to prepare the graft 156, depending on, for example, a patient's condition, an activity plan from now on, or the like. Various ways to consider selection of the tendon to be implanted are present, but are known, and hence descriptions thereof are omitted here.

The surgeon disposes the distal end of the arthroscope 22 in the joint cavity 136 of the knee joint 100 of the patient through the first cannula 18*a*. The surgeon uses the perfusion device 16 to fill the joint cavity 136 of the knee joint 100 of the patient with the saline while sucking the inside of the joint cavity. In this state, the surgeon suitably observes the inside of the joint cavity 136 of the knee joint 100 by use of the arthroscope 22.

The surgeon disposes the treating portion 68 of the ultrasonic treatment device 32 in the joint cavity 136 of the knee joint 100 of the patient through the second cannula 18*b*. As required, the surgeon excises the inflamed region of the synovial membrane 134 and the damaged region of the meniscus 142 or 144 as described above. In addition, the surgeon appropriately treats regions to which the osteochondritis dissecans are caused in the femur 112, the tibia 114 and the patella 118.

Figure 11A:
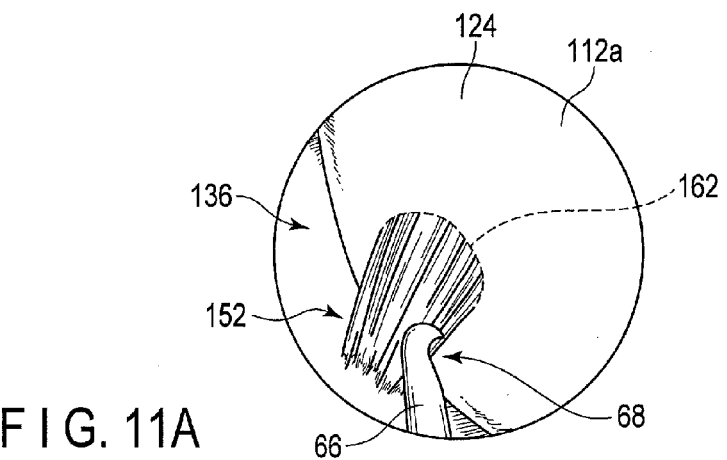
FIG. 11A is a schematic view showing a state where the ultrasonic vibration is transmitted to the treating portion of the ultrasonic treatment device to dissect the anterior cruciate ligament of a femur side of the knee joint under the arthroscope.

The arthroscope 22 passed through the first cannula 18*a* is moved to the posterior side of the knee joint 100, to confirm a remaining region of the anterior cruciate ligament 152 to the cartilage 112*a* of the lateral condyle 124 of the femur 112. As shown in FIG. 11A, the surgeon confirms a footprint region (an anatomical position to which the anterior cruciate ligament 152 adheres) 162 of the anterior cruciate ligament 152 on a femur 112 side with the arthroscope 22, and also confirms a ridge (bone ridge) 162*a* (see FIG. 11B) of the start region of the anterior cruciate ligament 152. Further, the treatment of the remaining region of the anterior cruciate ligament 152 to the cartilage 112*a* on the femur 112 side is performed with the ultrasonic treatment device 32. That is, as shown in FIG. 11A, the ridge 162*a* of the start region of the anterior cruciate ligament 152 is dissected in a state shown in FIG. 11B, by moving the treating portion 68 along the axial direction of the probe 66 while transmitting the ultrasonic vibration to the treating portion 68 of the ultrasonic treatment device 32. Specifically, as shown in FIG. 11A, the treating portion 68 of the ultrasonic treatment device 32 is disposed to abut on the remaining region of the anterior cruciate ligament 152, and the treating portion 68 is moved along the axial direction of the probe 66 while transmitting the ultrasonic vibration to the treating portion 68 of the ultrasonic treatment device 32, thereby resecting the remaining region. At this time, the treating portion 68 of the ultrasonic treatment device 32 can simultaneously cut off a soft tissue of the remaining region of the anterior cruciate ligament 152 and the hard tissue of the femur 112. In consequence, the ultrasonic treatment device 32 does not have to be replaced to the second cannula 18*b*.

Figure 11B:
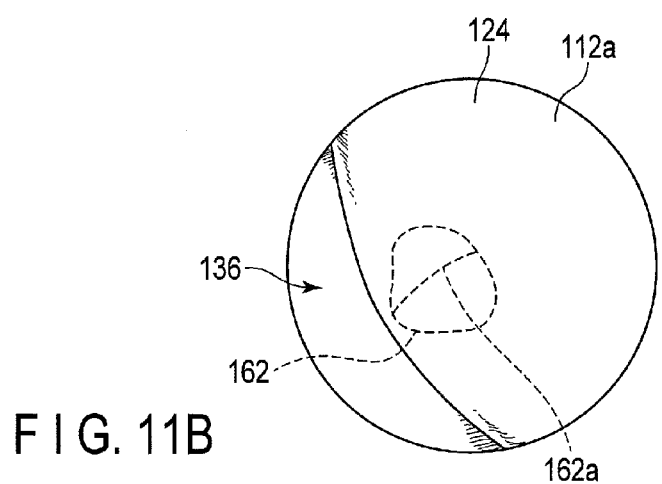
FIG. 11B is a schematic view showing a state where the ultrasonic vibration is transmitted to the treating portion of the ultrasonic treatment device to dissect the anterior cruciate ligament of the femur side of the knee joint under the arthroscope, thereby exposing a footprint region (a region to which the anterior cruciate ligament is attached)
Figure 11C:
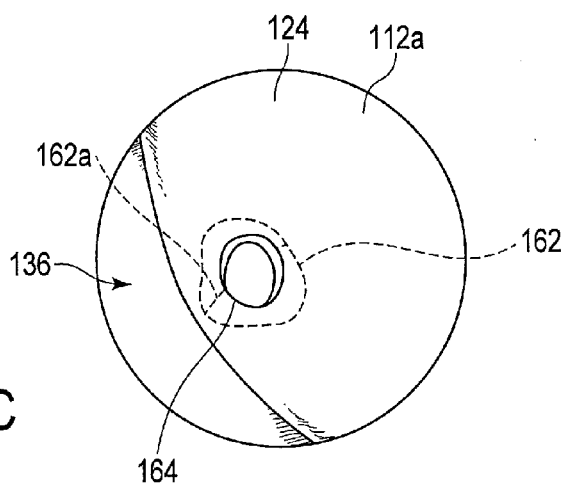
FIG. 11C is a schematic view showing a state where a concave hole (a concave region) is formed from the footprint region toward a lateral surface of a lateral condyle of the femur with the treating portion of the ultrasonic treatment device from which the ultrasonic vibration is transmitted to the footprint region of the anterior cruciate ligament of the femur side of the knee joint under the arthroscope.

As shown in FIG. 11B, a position of the footprint region 162 at which the start region of the removed anterior cruciate ligament 152 has been present is confirmed with the arthroscope 22 again. This position of the footprint region 162 is to be a position of one end of a tunnel 166 on the femur 112 side. To clarify the position of the one end of the tunnel 166, a part of the footprint region 162 of the anterior cruciate ligament 152 of the femur 112 is resected with the treating portion 68 of the ultrasonic treatment device 32 to which the ultrasonic vibration is transmitted, to form a concave hole 164 of a suitable depth shown in FIG. 11C. The surgeon uses the concave hole 164 as an auxiliary hole (a guiding hole) to form the tunnel 166 at a desirable position by an after-mentioned drill. In addition, the surgeon uses the concave hole 164 as a marking. The concave hole 164 is formed from a region to which the ligament 152 has adhered (the footprint region) toward a lateral surface of the lateral condyle 124 of the femur 112.

The probe 66 of the ultrasonic treatment device 32 can be formed into the suitable shape, and the treating portion 68 can be formed to be smaller than the shaver or the abrader burr. Consequently, in the treatment in which the ultrasonic treatment device 32 is used, the movable range to the cannula 18*b* can be increased, and a treatment region such as the footprint region 162 in which the start region of the anterior cruciate ligament 152 of the femur 112 has been present can more easily be approached as compared with the case where the shaver or the abrader burr is used. Additionally, the treating portion 68 of the ultrasonic treatment device 32 can simultaneously resect a remaining ligament and the femur 112. Consequently, when the surgeon performs the treatment by use of the ultrasonic treatment device 32 according to this embodiment, inserting and removing of the treatment device through the second cannula 18*b*, e.g., replacing of the shaver to remove the soft tissue with the abrader burr to remove the hard tissue can be eliminated.

Afterward, as shown in FIG. 12A, the surgeon moves the arthroscope 22 passed through the first cannula 18*a* to an anterior side of the knee joint 100, to confirm the remaining region of the anterior cruciate ligament 152 to the cartilage 114*a* on a tibia 114 side in the same manner as in the femur 112 side. As shown in FIG. 12A, the surgeon confirms a footprint region (an anatomical position to which the anterior cruciate ligament 152 adheres) 172 of the anterior cruciate ligament 152 on the tibia 114 side with the arthroscope 22. Further, a treatment of the remaining region of the anterior cruciate ligament 152 to the cartilage 114*a* on the tibia 114 side is performed with the ultrasonic treatment device 32. That is, as shown in FIG. 12A, the end region of the anterior cruciate ligament 152 is dissected in a state shown in FIG. 12B, by moving the treating portion 68 along the axial direction of the probe 66 while transmitting the ultrasonic vibration to the treating portion 68 of the ultrasonic treatment device 32. Specifically, as shown in FIG. 12A, the treating portion 68 of the ultrasonic treatment device 32 is disposed to abut on the remaining region of the anterior cruciate ligament 152, and the treating portion 68 is moved along the axial direction of the probe 66 while transmitting the ultrasonic vibration to the treating portion 68 of the ultrasonic treatment device 32, thereby resecting the remaining region. At this time, the treating portion 68 of the ultrasonic treatment device 32 can simultaneously cut off the soft tissue of the remaining region of the anterior cruciate ligament 152 and the hard tissue of the tibia 114. In consequence, the ultrasonic treatment device 32 does not have to be replaced to the second cannula 18*b*.

As shown in FIG. 12B, a position of the footprint region 172 at which the end region of the removed anterior cruciate ligament 152 has been present is confirmed with the arthroscope 22 again. This position of the footprint region 172 is to be a position of one end of a tunnel 176 on the tibia 114 side. To clarify the position of the one end of the tunnel 176, the footprint region 172 of the anterior cruciate ligament 152 of the tibia 114 is resected with the treating portion 68 of the ultrasonic treatment device 32 to which the ultrasonic vibration is transmitted, to form a concave hole 174 of a suitable depth shown in FIG. 12C. The surgeon uses the concave hole 174 as an auxiliary hole (a guiding hole) to form the tunnel 176 at a desirable position by the after-mentioned drill. In addition, the surgeon uses the concave hole 174 as a marking. The concave hole 174 is formed from the region to which the ligament 152 has adhered (the footprint region) toward a medial surface of a rough surface of the tibia 114.

The ultrasonic treatment device 32 is removed from the second cannula 18*b* after these treatments are ended.

Figure 13A:
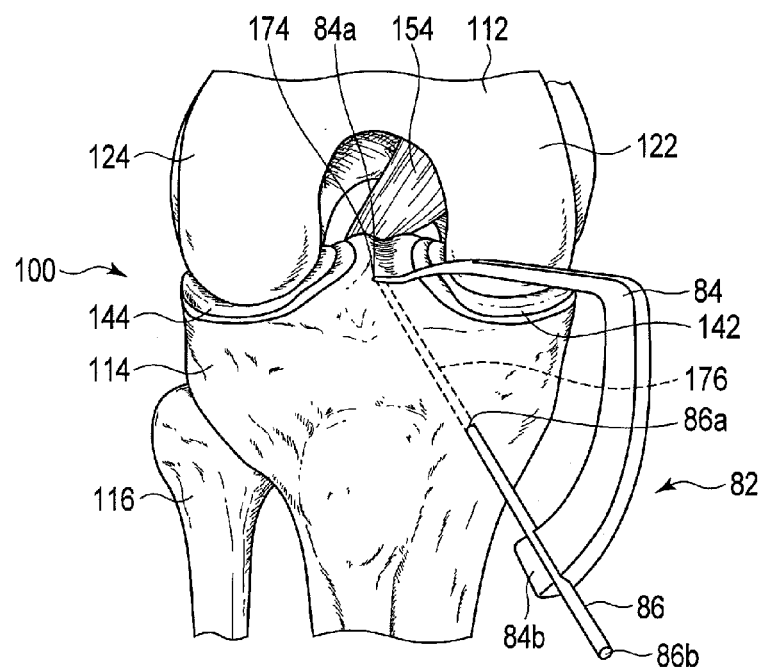
FIG. 13A is a schematic view showing a state where one end of an instrument that guides a drill to form a tunnel in a tibia is disposed in the footprint region of the anterior cruciate ligament of the tibia side of the knee joint or the concave hole formed in the footprint region, and the drill can be guided from the other end present on an outer rough surface side of the tibia toward the one end.
Figure 13B:
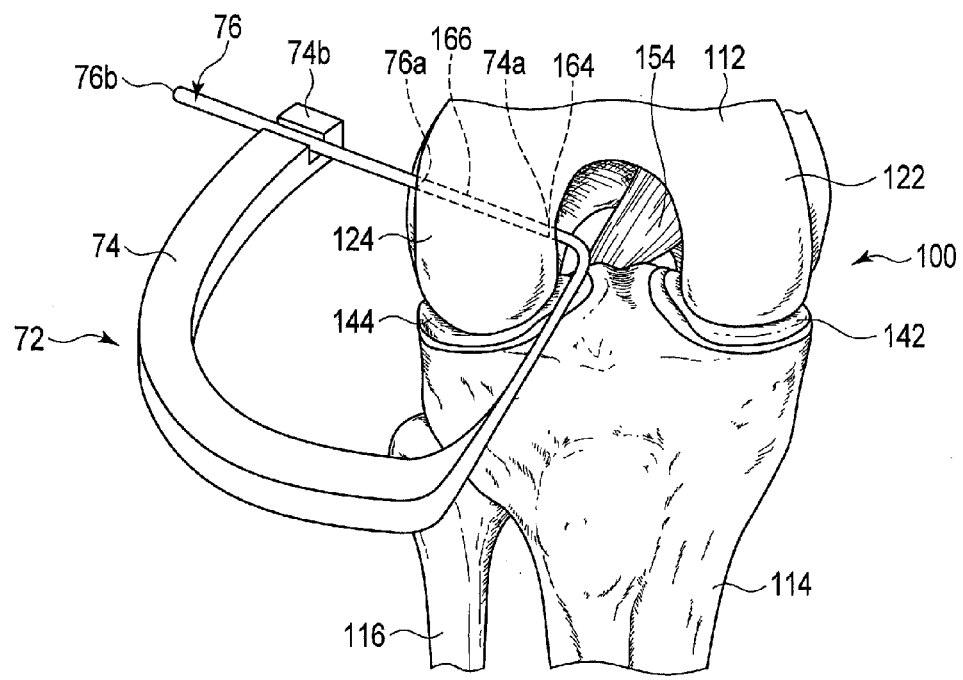
FIG. 13B is a schematic view showing a state where one end of an instrument that guides a drill to form a tunnel in a femur is disposed in the footprint region of the anterior cruciate ligament of the femur side of the knee joint or the concave hole formed in the footprint region, and the drill can be guided from the other end thereof on an outer side of the femur toward the one end.

Afterward, as shown in FIG. 13A, the surgeon forms a small hole in the tibia 114 by use of, for example, a wire-shaped first drill, and enlarges a diameter of the hole by a second drill having a larger diameter in accordance with a cross section of the graft 156 to form the tunnel 176 in the tibia 114. Similarly, as shown in FIG. 13B, the tunnel 166 is formed in the femur 112.

Here, for the purpose of forming the tunnel 166, an instrument 72 that guides the drill (not shown) is used. The instrument 72 has a main body 74 and a guiding tube 76 that guides the drill toward one end 74*a* of the main body 74.

The surgeon forms the concave hole 164 at one end of a position to form the bone tunnel 166 in the femur 112 with the treating portion 68 of the ultrasonic treatment device 32. Consequently, for example, the one end 74*a* of the main body 74 of the instrument 72 that guides the drill to form the bone tunnel 166 is fixed to the concave hole 164 through the portal 104 from which the second cannula 18*b* is pulled out, immediately before the bone tunnel 166 is formed.

The guiding tube 76 of the instrument 72 is supported at the other end 74*b* of the main body 74. At this time, in the main body 74, a distal end 76*a* of the guiding tube 76 is directed toward the one end 74*a* of the main body 74. That is, the distal end 76*a* of the guiding tube 76 is disposed toward the concave hole 164. Further, the surgeon passes the guiding tube 76 supported at the other end 74*b* of the main body 74, in a direction from the lateral side of skin of the right knee toward the one end 74*a* of the main body 74. The distal end 76*a* of the guiding tube 76 is disposed to abut on a lateral side of the lateral condyle 124 of the femur 112. It is to be noted that, when the concave hole 164 is used as a supporting point, the distal end 76*a* of the guiding tube 76 is passed from a suitable position of the lateral side of the skin of the right knee, to be supported at a suitable position of the lateral side of the lateral condyle 124 of the femur 112. Further, the unshown drill is guided from a proximal end 76*b* of the guiding tube 76 toward the distal end 76*a* of the guiding tube 76. The bone tunnel 166 is formed by the drill toward the one end 74*a* of the main body 74 from a state where the distal end of the drill is disposed to abut on the outer side of the lateral condyle 124 of the femur 112. In consequence, the bone tunnel 166 is formed from the outer side of the skin toward the concave hole 164. At this time, the one end 74*a* of the main body 74 of the instrument 72 is applied to the concave hole 164 of the femur 112, and hence one end of the bone tunnel 166 is easily formed at an anatomically correct position to the femur 112. That is, the concave hole 164 of the femur 112 is used as the supporting point to form the bone tunnel (tunnel) 166 between the concave hole 164 of the femur 112 and the outer surface of the lateral condyle 124 of the femur 112. Afterward, the second drill having a larger diameter than the first drill is moved along the first drill to suitably enlarge the tunnel 166 in accordance with an outer diameter of the graft 156.

Here, for the purpose of forming the bone tunnel 176, an instrument 82 that guides the drill (not shown) is used. The instrument 82 has a main body 84 and a guiding tube 86 that guides the drill toward one end 84*a* of the main body 84.

In addition, the surgeon forms the concave hole 174 at one end of a position to form the bone tunnel 176 in the tibia 114 with the treating portion 68 of the ultrasonic treatment device 32. Consequently, for example, the one end 84*a* of the main body 84 of the instrument 82 that guides the drill to form the tunnel 176 is fixed to the concave hole 174 through the portal 104 from which the second cannula 18*b* is pulled out, immediately before the bone tunnel 176 is formed.

The guiding tube 86 of the instrument 82 is supported at the other end 84*b* of the main body 84. At this time, in the main body 84, a distal end 86*a* of the guiding tube 86 is directed toward the one end 84*a* of the main body 84. That is, the distal end 86*a* of the guiding tube 86 is disposed toward the concave hole 174. Further, the surgeon passes the guiding tube 86 supported at the other end 84*b* of the main body 84, in a direction from the lateral side of the skin of the right knee toward the one end 84*a* of the main body 84. The distal end 86*a* of the guiding tube 86 is disposed to abut on a rough surface of a front surface of the tibia 114. It is to be noted that, when the concave hole 174 is used as the supporting point, the distal end 86*a* of the guiding tube 86 is passed from a suitable position of the lateral side of the skin of the right knee, to be supported at a suitable position of the outer side of the rough surface of the tibia 114. Further, the unshown drill is guided from a proximal end 86*b* of the guiding tube 86 toward the distal end 86*a* of the guiding tube 86. The bone tunnel 176 is formed by the drill toward the one end 84*a* of the main body 84 from a state where the distal end of the drill is disposed to abut on the lateral side of the rough surface of the tibia 114. In consequence, the bone tunnel 176 is formed from the lateral side of the skin toward the concave hole 174. At this time, the one end 84*a* of the main body 84 of the instrument 82 is applied to the concave hole 174 of the tibia 114, and hence one end of the bone tunnel 176 is easily formed at an anatomically correct position to the tibia 114. That is, the concave hole 174 of the tibia 114 is used as the supporting point to form the bone tunnel 176 between the concave hole 174 of the tibia 114 and the rough surface of the tibia 114. Afterward, the second drill having a larger diameter than the first drill is moved along the first drill, to suitably enlarge the bone tunnel 176 in accordance with the outer diameter of the graft 156.

For example, when a position to which an end of the anterior cruciate ligament 152 has adhered is dissected by using the abrader burr, it has been difficult to form the concave hole due to the problem of accessibility or the problem that treatment time is lengthened. Here, the concave holes 164 and 174 are suitably formed by using the ultrasonic treatment device 32, and hence the one end of each of the known instruments 72 and 82 that guide the first drill to form the bone tunnels 166 and 176 can exactly be positioned. Consequently, the bone tunnels 166 and 176 can exactly be prepared more easily than before, in a state where the instrument is matched with each of the ends (the start region and the end region) of the anterior cruciate ligament 152 before damaged, to the femur 112 and the tibia 114.

Figure 14:
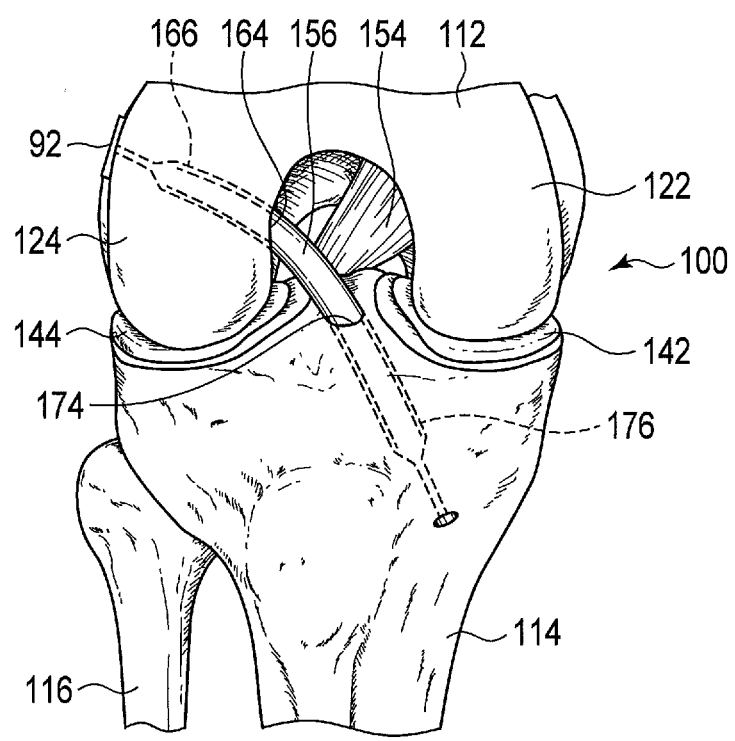
FIG. 14 is a schematic view showing a state where a graft is interposed between a tunnel on the femur side and a tunnel on the tibia side to fix end portions of the graft to outer sides of the femur and the tibia, respectively.

The instruments 72 and 82 and the like are removed, and then, as shown in FIG. 14, the graft 156 prepared in advance is inserted through the bone tunnels 166 and 176 into the joint cavity 136 of the knee joint 100, to fix the one end of the graft 156 to the lateral side of the lateral condyle 124 of the femur 112 and to fix the other end of the graft to the rough surface of the tibia 114. At this time, the graft 156 may be inserted from the femur 112 side toward the tibia 114 side, or may be inserted from the tibia 114 side toward the femur 112 side. One of the one end and the other end of the graft 156 is fixed with a fixing tool 92.

As described above, the technique of excising the damaged region of the anterior cruciate ligament 152 under the arthroscope 22 and the technique of reconstructing the anterior cruciate ligament 152 can be considered as follows.

By use of the treatment system 10, a series of treatment of removing the damaged anterior cruciate ligament 152 and exposing the footprint regions 162 and 172 can be performed with the treating portion 68 of the treatment device 32, while the one ultrasonic treatment device 32 is disposed as it is in the second cannula 18b. The surgeon has heretofore replaced and used different instruments to the portal 104 by, for example, using the shaver or the like in a removing treatment of the remaining ligament of the anterior cruciate ligament 152 and using the abrader burr or the like in the smoothening treatment (the exposing treatment) of the footprint regions 162 and 172 of the hard tissue. When the remaining ligament of the anterior cruciate ligament 152 and the treatment object regions of the footprint regions 162 and 172 are removed, the ultrasonic treatment device 32 does not have to be replaced to the portal 104. These treatments can be performed with the one ultrasonic treatment device 32. Consequently, during the surgical treatment, the surgeon does not have to replace the treatment device 32 disposed in the joint cavity 136, and hence the surgical treatment time can be shortened.

In addition, the footprint regions 162 and 172 are dissected, and simultaneously, the concave holes 164 and 174 can be formed with the treating portion 68 of the ultrasonic treatment device 32 without replacing the tool. In consequence, the one end of each of the instruments 72 and 82 to suitably form the bone tunnels 166 and 176 can easily be positioned to the concave holes 164 and 174.

When the bone tunnels 166 and 176 are formed by utilizing the concave holes 164 and 174 prepared by using an ultrasonic output under the arthroscope 22, shift of the one end of each of the instruments 72 and 82 can be prevented, and hence the bone tunnels 166 and 176 can more exactly be prepared at the correct positions. At this time, the concave holes 164 and 174 are prepared and the concave holes 164 and 174 are utilized, and hence the bone tunnels 166 and 176 can be formed at the correct positions without necessarily using an X-ray.

The probe 66 of the ultrasonic treatment device 32 can be formed into the suitable shape, and the treating portion 68 can be formed to be smaller than the shaver or the abrader burr. Consequently, in the treatment in which the ultrasonic treatment device 32 is used, the movable range to the cannula 18b can be increased, and a treatment region such as the rear side of the knee joint 100 can more easily be approached as compared with the case where the shaver or the abrader burr is used. Additionally, in the treatment of the ultrasonic treatment device 32, the more precise and smoother treated surface can be formed than in the case where the shaver or the abrader burr is used. Consequently, when the surgeon performs the treatment by use of the ultrasonic treatment device 32 and then the patient bends and stretches the knee joint 100 to move the femur 112, the tibia 114 and the patella 118, the femur 112, the tibia 114 and the patella 118 can be prevented from being stuck on one another, which can contribute to the smooth joint movement.

The abrader burr abrades the bone that is the hard tissue by the periaxial rotation, and hence the loads that act on the abrader burr increase in a case where the bone is abraded. Consequently, the abrader burr might noticeably entirely be vibrated by the loads onto the treating portion. On the other hand, the treating portion 68 of the ultrasonic treatment device 32 is not periaxially rotated but the bone can be resected only by moving (vibrating) the treating portion in the axial direction of the probe 66. Consequently, the loads that act on the housing 62 or the like through the treating portion 68 are small in a case where the bone is resected by the treating portion 68. In consequence, the ultrasonic treatment device 32 inserted into the joint cavity 136 of the knee joint 100 through the portal 104 does not noticeably vibrate. That is, in the case where the bone is resected by the treating portion 68, the leaping of the treating portion 68 is not caused by the rotary motion as in the abrader burr, and hence the damages of the peripheral tissue can be decreased.

In addition, the surgeon uses the ultrasonic treatment device 32 and hence does not have to use the high frequency device. When the treatment is performed by using the high frequency device, there is the fear that the surface is invaded by heat. On the other hand, when the ultrasonic treatment device 32 is used, the normal regions of the cartilages 112a and 114a of the femur 112 and the tibia 114 are less invaded by heat, and the thermal necrosis is prevented from being caused to the cartilages 112a and 114a.

It is to be noted that the concave holes 164 and 174 do not necessarily have to be formed. When the concave hole 164 is not formed, one end of the instrument 72 that guides the drill to form the bone tunnel 166 is disposed in the footprint region 162 of the anterior cruciate ligament 152 of the femur 112, to form the bone tunnel 166 in the femur 112. That is, the footprint region 162 is used as the supporting point in place of the concave hole 164, to form the bone tunnel 166 in the femur 112 by use of the instrument 72. Similarly, when the concave hole 174 is not formed, one end of the instrument 82 that guides the drill to form the bone tunnel 176 is disposed in the footprint region 172 of the anterior cruciate ligament 152 of the tibia 114, to form the bone tunnel 176 in the tibia 114. That is, the footprint region 172 is used as the supporting point in place of the concave hole 174, to form the bone tunnel 176 in the tibia 114 by use of the instrument 82.

Here, an order to prepare the bone tunnels 166 and 176 is described in order of the femur 112 and the tibia 114, but, needless to say, the order may be reversed, i.e., the order may be the tibia 114 and then the femur 112.

In addition, here, there is described the example where the anterior cruciate ligament 152 is reconstructed, but also when the posterior cruciate ligament 154 is reconstructed, the treating portion 68 of the ultrasonic treatment device 32 can similarly simultaneously cut off the soft tissue of the remaining region of the posterior cruciate ligament and the hard tissue of the femur 112. In consequence, the footprint region of the posterior cruciate ligament 154 on the femur 112 side can easily be confirmed by using the arthroscope 22. Similarly, the treating portion 68 of the ultrasonic treatment device 32 can simultaneously cut off the soft tissue of the remaining region of the posterior cruciate ligament 154 and the hard tissue of the tibia 114. In consequence, the footprint region of the posterior cruciate ligament 154 on the tibia 114 side can easily be confirmed by using the arthroscope 22. In addition, the concave holes 164 and 174 can easily be formed under the arthroscope 22 by moving the treating portion 68 along the axial direction of the probe 66 while transmitting the ultrasonic vibration to the treating portion 68 of the ultrasonic treatment device 32, to the footprint regions of the posterior cruciate ligaments 154 of the femur 112 and the tibia 114 in the same manner as in the footprint regions 162 and 172 of the anterior cruciate ligament 152.

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. A surgical treatment of an anterior cruciate ligament or a posterior cruciate ligament of a knee joint which is to be performed under an arthroscope, the surgical treatment comprising:

inserting the arthroscope and a treating portion of an ultrasonic device into a knee joint cavity;

bringing the treating portion of the ultrasonic device into contact with a start region to which the anterior cruciate ligament or the posterior cruciate ligament of a femur adheres, and excising the femur and a remaining ligament of the anterior cruciate ligament, or the femur and a remaining ligament of the posterior cruciate ligament by ultrasonically vibrating the treating portion, thereby exposing a footprint region of the femur; and bringing the treating portion of the ultrasonic device into contact with an end region to which the anterior cruciate ligament or the posterior cruciate ligament of a tibia adheres, and excising the tibia and a remaining ligament of the anterior cruciate ligament, or the tibia and a remaining ligament of the posterior cruciate ligament by ultrasonically vibrating the treating portion, thereby exposing a footprint region of the tibia.

2. The surgical treatment according to claim 1, comprising forming a tunnel between the footprint region of the tibia and a lateral side of a rough surface of the tibia using the footprint region of the tibia as a supporting point.

3. The surgical treatment according to claim 1, comprising forming a tunnel between the footprint region of the femur and a lateral surface of a lateral condyle of the femur using the footprint region of the femur as a supporting point.

* * * * *